United States Patent [19]

Hsiao et al.

[11] Patent Number: 4,853,333
[45] Date of Patent: Aug. 1, 1989

[54] PRODUCTION OF ROTAVIRUS IN YEAST

[75] Inventors: Chu-lai Hsiao, Wilmington, Del.; Bruce B. Mason, St. Davids; Alan R. Davis, Wayne, both of Pa.

[73] Assignee: American Home Products Corporation, New York, N.Y.

[21] Appl. No.: 759,546

[22] Filed: Jul. 26, 1985

[51] Int. Cl.⁴ .................... C12N 15/00; C12N 5/00; C12P 21/00
[52] U.S. Cl. .................................. 435/256; 435/255; 435/68; 435/70; 435/172.3; 435/320; 935/28; 935/29; 935/56; 935/65; 935/69
[58] Field of Search ................ 435/68, 70, 172.3, 256, 435/255, 317, 948, 235, 320; 935/28, 29, 56, 65, 73, 69

[56] References Cited

PUBLICATIONS

Both et al, *Proc. Natl. Acad. Sci.*, vol. 80, pp. 3091–3095, May 1983, "Serotype-Specific Glycoprotein of Simian 11 Rotavirus: Coding Assignment and Gene Sequence".
Bennetzen et al, *J. Biol. Chem.*, vol. 257(6), Mar. 25, 1982, pp. 3018–3025, "The Primary Structure of the *Saccharomyces Cerevisiae* Gene for Alcohol Dehydrogenase I".
Gunn et al., *J. Virol.*, Jun. 1985, pp. 791–797, vol. 54(3), "Rotavirus Neutralizing Protein VP7: Antigenic Determinants Investigated by Sequence Analysis and Peptide Synthesis".
Kouvelos et al., *J. Gen. Virol.*, vol. 65, 1984, pp. 1211–1214, "Comparison of Bovine, Simian and Human Rotavirus Structural Glycoproteins".
Glass et al, *Virology*, vol. 141, pp. 292–298, 1985, "Nucleotide Sequence of the Structural Glycoprotein VP7 Gene of Nebraska Calf Diarrhea Virus Rotavirus: Comparison with Homogolous Genes from Four Strains of Human and Animal Rotaviruses".
Richardson et al, *J. Virol.*, Sep. 1984, pp. 860–862, vol. 51(3), "Nucleotide Sequence of the Gene Encoding the Serotype-Specific Antigen of Human (Wa) Rotavirus: Comparison . . . UK Bovine Rotaviruses".
Broach et al, Gene, vol. 8, 1979, pp. 121–133, "Transformation in Yeast: Development of a Hybrid Cloning Vector and Isolation of the CAN 1 Gene".
Kalica et al, *Virology*, vol. 112, pp. 385–390, 1981, "Genes of Human (Strain Wa) and Bovine (UK) Rotaviruses That Code for Neutralization and Subgroup Antigens".
McKnight et al, *Proc. Natl. Acad. Sci.*, vol. 80, pp. 4412–4416, Jul. 1983, "Selection of Functional cDNAs by Complementation in Yeast".
Ammerer, *Methods in Enzymol*, vol. 101, pp. 192–201, 1983, "Expression of Genes in Yeast Using the ADC1 Promotor".

*Primary Examiner*—Robin Teskin
*Attorney, Agent, or Firm*—George Tarnowski

[57] ABSTRACT

There is disclosed a DNA transfer vector capable of replication in either a yeast cell or a bacterial cell and having inserted therein a DNA segment coding for human WA rotavirus surface antigen VP7. The transfer vector carrying the foreign DNA is used to transform yeast cells in order to produce the surface antigen VP7 which is capable of eliciting in vivo production of neutralizing antibodies with respect to human WA rotavirus. The surface antigen VP7 so elaborated and its use in a pharmaceutical vaccine composition are also disclosed.

2 Claims, 7 Drawing Sheets

Figure 1

```
GGCTTTAAAAGAGAGAATTTCCGTCTGGCTAACGGTTAGCTCCTTTTAATG TAT GGT ATT GAA TAT ACC ACA
                                                    MET TYR GLY ILE GLU TYR THR THR
ATT CTA ATC TTT TTG ATA TCA ATC ATT CTA CTC AAC TAT ATA TTA AAA TCA GTG ACT CGA
ILE LEU ILE PHE LEU ILE SER ILE ILE LEU LEU ASN TYR ILE LEU LYS SER VAL THR ARG
       10                             20
ATA ATG GAC TAC ATT ATA TAT AGA TTT TTG TTG ATT ACT GTA GCA TTA TTT GCT TTG ACA
ILE MET ASP TYR ILE ILE TYR ARG PHE LEU LEU ILE THR VAL ALA LEU PHE ALA LEU THR
    30                                40
AGA GCT CAG AAT TAT GGA CTT AAC TTA CCA ATA ACA GGA TCA ATG GAC GCT GTA TAT ACT
ARG ALA GLN ASN TYR GLY LEU ASN LEU PRO ILE THR GLY SER MET ASP ALA VAL TYR THR
        50                                60
AAC TCT ACT CAA GAA GAA GTG TTT CTA ACT TCT ACG TTA TGT CTG TAT TAT CCA ACT GAA
ASN SER THR GLN GLU GLU VAL PHE LEU THR SER THR LEU CYS LEU TYR TYR PRO THR GLU
 *      70                                80
GCA AGT ACT CAA ATC AAT GAT GGT GAC TGG AAA GAC TCA TTG TCG CAA ATG TTT CTT ACA
ALA SER THR GLN ILE ASN ASP GLY ASP TRP LYS ASP SER LEU SER GLN MET PHE LEU THR
        90                                100
AAG GGT TGG CCA ACA GGA TCT GTT TAC TTT AAA GAG TAC TCA AAT ATT GTT GAT TTT TCT
LYS GLY TRP PRO THR GLY SER VAL TYR PHE LYS GLU TYR SER ASN ILE VAL ASP PHE SER
        110                               120
GTT GAC CCA CAG CTG TAT TGT GAC TAT AAT TTA GTA CTT ATG AAA TAT GAC CAA AGT CTT
VAL ASP PRO GLN LEU TYR CYS ASP TYR ASN LEU VAL LEU MET LYS TYR ASP GLN SER LEU
        130                               140
AAA TTA GAT ATG TCA GAG TTA GCT GAT TTA ATA TTG AAT GAA TGG TTA TGT AAC CCA ATG
LYS LEU ASP MET SER GLU LEU ALA ASP LEU ILE LEU ASN GLU TRP LEU CYS ASN PRO MET
        150                               160
GAT GTA ACA TTA TAC TAT TAT CAA CAA TCG GGA GAA TCA AAT AAG TGG ATA TCG ATG GGA
ASP VAL THR LEU TYR TYR TYR GLN GLN SER GLY GLU SER ASN LYS TRP ILE SER MET GLY
        170                               180
TCA TCA TGT ACC GTG AAA GTG TGT CCG CTA AAT ACA CAA ACG TTA GGG ATA GGT TGT CAA
SER SER CYS THR VAL LYS VAL CYS PRO LEU ASN THR GLN THR LEU GLY ILE GLY CYS GLN
        190                               200
ACA ACA AAC GTA GAC TCA TTT GAA ATG ATT GCT GAG AAT GAG AAA TTA GCT ATA GTG GAT
THR THR ASN VAL ASP SER PHE GLU MET ILE ALA GLU ASN GLU LYS LEU ALA ILE VAL ASP
        210                               220
GTC GTT GAT GGG ATA AAT CAT AAA ATA AAT TTA ACA ACT ACG ACA TGT ACT ATT CGA AAT
VAL VAL ASP GLY ILE ASN HIS LYS ILE ASN LEU THR THR THR THR CYS THR ILE ARG ASN
        230                               240
TGT AAG AAA TTA GGT CCA AGA GAA AAT GTA GCT GTA ATA CAA GTT GGT GGT TCT AAT GTG
CYS LYS LYS LEU GLY PRO ARG GLU ASN VAL ALA VAL ILE GLN VAL GLY GLY SER ASN VAL
        250                               260
TTA GAC ATA ACA GCA GAT CCA ACA ACT AAT CCA CAA ACT GAG AGA ATG ATG AGA GTG AAT
LEU ASP ILE THR ALA ASP PRO THR THR ASN PRO GLN THR GLU ARG MET MET ARG VAL ASN
        270                               280
TGG AAA AAG TGG TGG CAA GTA TTT TAT ACT ATA GTA GAT TAT ATT AAT CAA ATT GTA CAG
TRP LYS LYS TRP TRP GLN VAL PHE TYR THR ILE VAL ASP TYR ILE ASN GLN ILE VAL GLN
        290                               300
GTA ATG TCC AAA AGA TCA AGA TCA TTA AAT TCT GCA GCT TTT TAT TAT AGA GTA TAG
VAL MET SER LYS ARG SER ARG SER LEU ASN SER ALA ALA PHE TYR TYR ARG VAL *** ATA
        310                               320
TATCTTAGATTAGAATTGTTCGATGTGACC
```

FIGURE 3
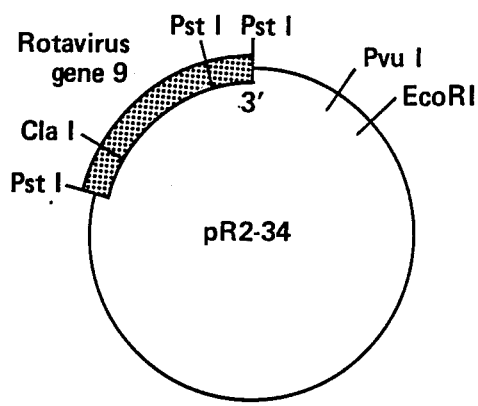
pR2-34
↓ Linearized the plasmid with restriction endonuclease Pvu I
↓ Digested with exonuclease Bal 31 to shorten the DNA
↓ Klenow DNA polymerase to fill in the end
↓ Addition of EcoRI linker and digested with EcoRI
↓ Ligated with T4 DNA ligase
↓ Transformation of E coli 294
↓ Screen individual clones for plasmids that have the right length
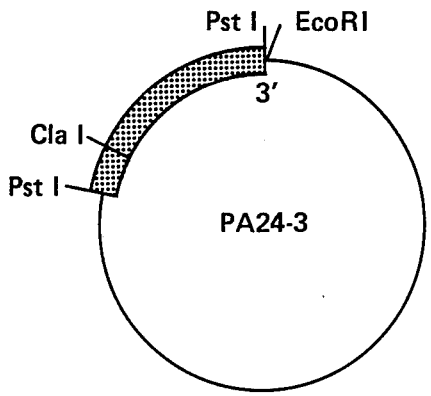
PA24-3

Arrow ( →  ) indicates direction of transcription.

PRODUCTION OF ROTAVIRUS IN YEAST

BACKGROUND OF THE INVENTION

Rotaviruses are the single most important cause of childhood viral gastroenteritis in the developed and developing countries. It is estimated that over one million diarrhea-related infantile deaths that occur annually are directly related to rotaviruses. The urgent need for a rotavirus vaccine has been recognized, but for a number of factors, such a vaccine is not yet commercially available. Among the problems encountered are the failure of adequate in vitro growth of some rotavirus strains, the uncertainty as to which strain(s) should be incorporated into a vaccine, the lack of a good experimental animal model system and a lack of effective efficacy studies in humans.

One recent approach to the development of a rotavirus vaccine involved the use of a live attenuated strain of a calf rotavirus which is immunologically distinct from human rotavirus strains, but which protects against human rotavirus infection, mainly of type I. It was found in one study that after oral immunization with such a vaccine, a severe case of diarrhea occurred prior to establishment of immunity. This was caused by a wild type rotavirus strain which interacted with the vaccine strain via gene reassortment to cause formation of a new reassortment virus. In other studies, although protection rates against diarrhea were over 80%, the protection rates against wild gastrointestinal infection and the seroconversion rate in vaccinated individuals were considerably lower. Moreover it has not been determined whether this vaccine can be effective against other rotavirus serotypes.

Other rotavirus vaccine programs include the use of a rhesus monkey rotavirus strain which is serologically related to human rotavirus type 3, and future studies are being designed to isolate a reassortment virus or viruses which contains the gene responsible for the type-specific antigen common to all four rotavirus serotypes.

BRIEF DESCRIPTION OF THE INVENTION

The present invention relates, in one aspect, to a novel plasmid which can replicate autonomously in yeast with inserted deoxyribonucleic acid (DNA) which codes for human rotavirus WA strain surface antigen VP7. This surface antigen is responsible for elicitation of neutralizing antibodies to rotavirus antigen. The novel plasmid can be introduced into a suitable yeast host which can then be cultured to produce the surface antigen protein product in the same manner as the manufacture of antibiotic compounds. The product when so produced in sufficient quantity and purified, can be formulated into an appropriate suspension vehicle for use as a rotavirus vaccine. The present invention, therefore, encompasses, in addition to the novel plasmid, the DNA segment coding for the VP7 surface antigen, the polypeptidic VP7 surface antigen, and a vaccine product prepared from said surface antigen.

BRIEF DESCRIPTION OF THE DRAWINGS

FIG. 1: depicts the nucleotide structure of human rotavirus WA strain gene 9 and the polypeptide chain resulting from the translation of the gene;

FIG. 3: depicts editing of the 3'-end half of gene 9;

DESCRIPTION OF THE INVENTION

Figure 2:
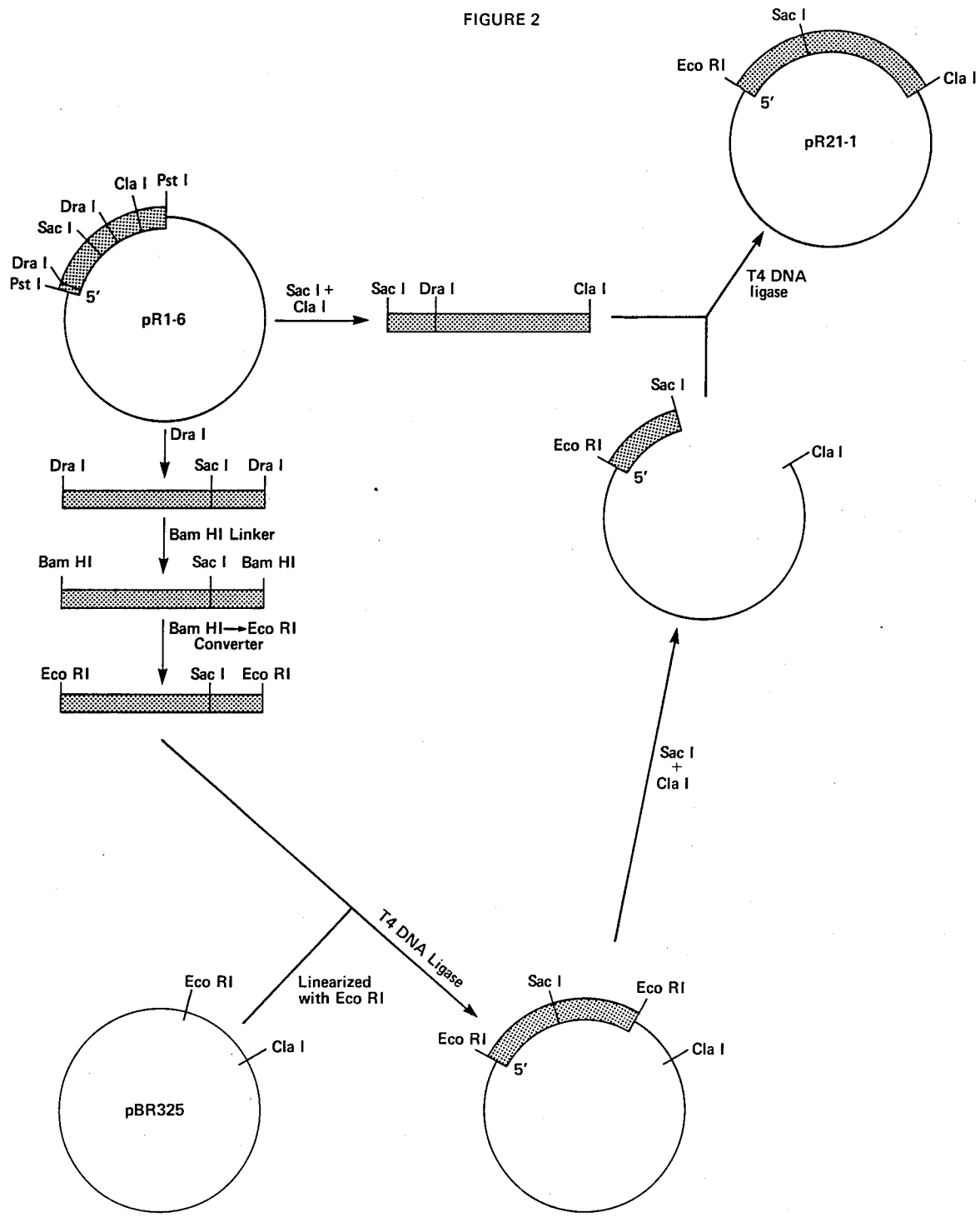
FIG. 2: depicts editing of the 5'-end half of gene 9.

In its basic outline, a method of endowing a yeast or another microorganism with the ability to synthesize a new protein involves three general steps: (1) isolation and purification of the specific gene or nucleotide sequence containing the genetically coded information for the amino acid sequence of the desired protein; (2) recombination of the isolated nucleotide sequence with an appropriate transfer vector, usually the DNA of a plasmid; and (3) transfer of the vector to the appropriate microorganism and selection of a strain of the recipient microorganism containing the desired genetic information.

In the present invention, there is first disclosed the preparation of complementary DNA (cDNA) having the nucleotide sequence which codes for rotavirus WA strain surface antigen VP7. The synthesis of this cDNA sequence is based on the cloning of double-stranded RNA segment of gene 9 of human rotavirus WA strain. The cDNA synthesized by the methods described herein may be inserted into the novel plasmid of the present invention and the plasmid vector so prepared may then be transferred into a suitable yeast host for culturing so as to produce human rotavirus surface antigen VP7.

The strategy for the cloning of gene 9 of human WA rotavirus is similar to that described by Cashdollar et al., *Proc. Natl. Acad. Sci. USA*, 79, 7644–48 (1982). According to this cloning scheme, gene 9 double-stranded RNA (dsRNA) of WA human rotavirus, isolated from a polyacrylamide gel, is denatured and tailed with polyadenylic acid, as per Sippel, A.E., *Eur. J. Biochem.*, 37, 31–40 (1973) to an average of 30 adenylate residues per single stranded RNA chain. The poly (A+)-RNA is then primed with oligo (dT) and treated with reverse transcriptase in the presence of dATP, dCTP, dGTP and dTTP to make cDNA, see Davis et al., *Gene*, 10, 205–218 (1980). Subsequently, the cDNA is extracted with phenol/chloroform, the aqueous phase is adjusted with NaOH and incubated. After neutralization, the cDNA is annealed followed by slow cooling. The cDNA is then repaired using either AMV reverse transcriptase or the Klenow fragment of DNA polymerase 1. The cDNA is fractionated on an alkaline agarose gel and the DNA's of approximately 1000 bp are eluted, tailed with dC residues using terminal transferase, see Davis et al., supra, and cloned into plasmid pBR322 that has been cut with PstI and tailed with dG residues. cDNA is prepared from small cultures of ampicillin sensitive colonies. Propagation is carried out in *E. coli* K12 strain 294 (ATCC No. 31446).

Characterization of the cDNA inserts by a combiation of restriction enzyme analysis and DNA sequencing results in the finding that pre-selection of fulllength gene 9 DNA results in production of cDNA clones with deletions and rearrangements. A full-length copy of WA gene 9 could not be obtained by the cloning. Thus, in order to sequence WA gene 9, two separate clones with overlapping ends were analyzed by the method of Maxam and Gilbert, *Methods Enzymol.*, 65, 499–560 (1980). The one clone, R2-34, contains the 3'-terminal half of gene 9, while the other clone, R1-6, contains the 5'-terminal half of gene 9. The overlap region of these clones is between nucleotide 565 and 663.

The sequence of the entire gene 9 is shown in FIG. 1. Postulated glycosylation sites are found at amino acids 69 and 238, which are marked with an asterisk. The WA rotavirus gene coding for surface antigen VP7 has a length of 1062 base pairs, and hybridization of cloned DNA coding for VP7 to gene segment 9 of WA rotavirus substantiates that the ninth segment of WA rotavirus codes for VP7.

Because the cDNA of WA rotavirus gene 9 cloned in two pieces in separate plasmids, it was necessary to reconstruct the gene before it could be inserted into a suitable vector for transfection into yeast. Both sections of the gene 9 cDNA were modified to remove the poly A and poly C tails which were put onto the cDNA during cloning of gene 9. Additionally, it is necessary to process the WA gene 9 cDNA segments in order to remove extraneous sequences prior to expressing it in an eucaryotic vector.

The method used to modify the 5'-end is depicted in FIG. 2. In its essentials, the 5'-end of WA gene 9 was excised from the R1-6 plasmid DNA with DraI. Synthetic linkers (Bam HI) were ligated to the ends of the fragments and then cloned into the Bam HI site of pBR322. The BAM HI fragment was extracted from this clone and Bam HI-EcoRI convertors were added to the ends and the fragment was ligated into the EcoRI site of pBR325. This chimeric plasmid was digested with SacI and ClaI and the SacI-ClaI fragment from the original R1-6 clone was then ligated into this chimeric vector, which resulted in a complete clone of the 5'-end of the WA gene 9 (R21-1).

The method used to modify the 3'-end is depicted in FIG. 3. The plasmid R2-34 is digested with restriction enzyme PvuI to generate a linear molecule. Exonuclease Bal31 is used to shorten the linearized molecule from both ends. The reaction is stopped at the appropriate time and then treated with Klenow DNA polymerase to fill in the end. After addition of EcoRI linker, the plasmid is reclosed with T4 DNA ligase. Following this manipulation, the DNA is transfected into *E. coli* K12 strain 294 and the individual colonies are screened for plasmids bearing the correct sequence length. The clone ending 3 base pairs behind the translation termination codon (TAG) is used in the final reconstruction of rotavirus gene 9.

Figure 4:
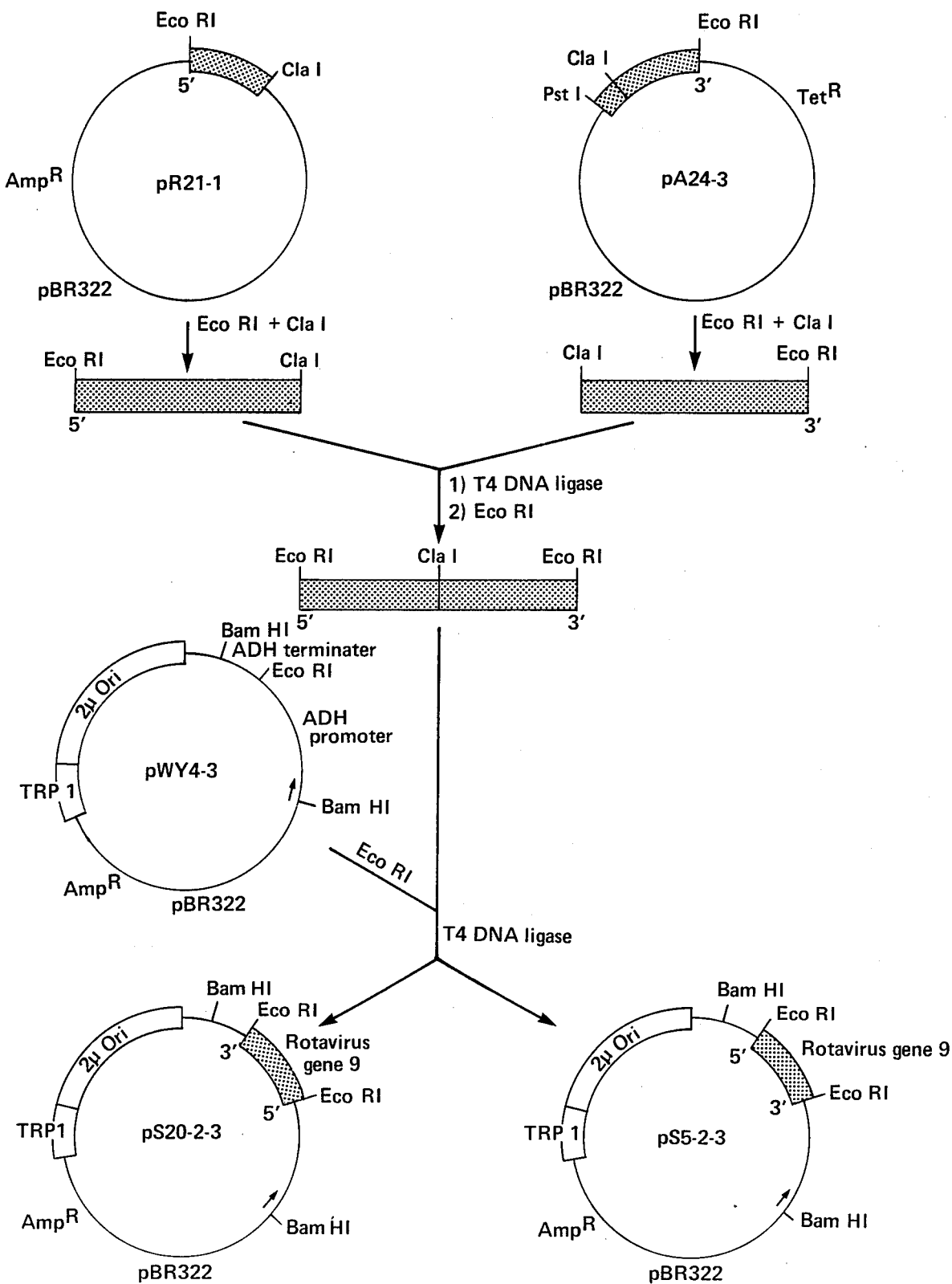
FIG. 4: depicts reconstruction of entire gene 9 from the edited 5'-end and 3'-end halves and its insertion into yeast expression vector pWY4-3.

The reconstruction of the full-length WA gene 9 from the 5'-end and 3'-end is depicted in FIG. 4. In this reconstruction, the EcoRI-ClaI fragment of the 5'-end and the ClaI-EcoRI fragment of the 3'-end of gene 9 are isolated and ligated with T4 DNA ligase. The 1.0 Kb EcoRI fragment which has the complete gene 9 sequence is isolated and then inserted into the novel shuttle expression vector of the invention and transformed in *E. coli* K12 strain 294. Screening of the transformants yields recombinant plasmids that have the gene 9 inserted in both orientations. Both types of plasmids are transfected into yeast to check for the production of surface antigen VP7. pS20-2-3 contains rotavirus gene 9 in the correct orientation.

For maximal expression of foreign genes in microbial systems, it is usually advantageous to use homologous regulating elements within the expression vector. Efficiency of expression (product formation) is believed to be a function of and proportional to the strength of the promoter employed. Those fragments of DNA in expression plasmids which contain sequences with strong transcription-promoting activity are called "promoters." They are ideal components of DNA vectors for commercial production of large quantities of protein coded by foreign genes under their transcripional control. The other necessary component of an expression vector is an appropriate terminator, so that the expression vector contains a promoter—foreign gene—terminator sequence. The presence of the terminator increases expression of the foreign DNA. Accordingly, the novel plasmid of the present invention is a yeast expression vector into which can be inserted the segment of cDNA coding for human rotavirus WA surface antigen VP7, and which is under transcriptional control of a yeast alcohol dehydrogenase (ADH) gene promoter and terminator sequence [Bennetzen and Hall, *J. Biol. Chem.*, 257, 3018–3025 (1982)]. This expression vector, when used to transform yeast cells, yields substantial amounts of the VP7 surface antigen coded by the cDNA segment insert therein.

Figure 5:
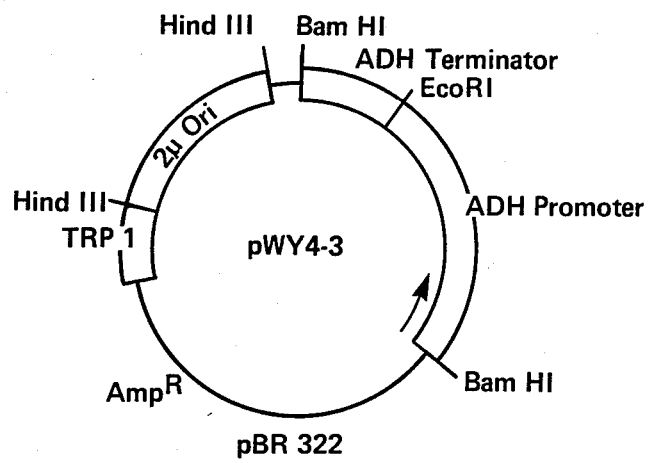
FIG. 5: depicts the novel yeast expression vector pWY4-3 of the invention.

FIG. 5 depicts the yeast expression plasmid of the invention. The most appropriate DNA vector for the construction of the novel plasmid of the invention is a shuttle vector. These vectors can "shuttle" between a bacterial strain, such as *E. coli*, and yeast, since they have a bacterial origin of replication and a yeast origin of replication, e.g. Ammerer et al., *Recombinant DNA, Proc. Third Cleveland Symposium Macromolecules*, (Walton, A.G., ed.), Elsevier, Amsterdam (1981). A typical bacterial origin of replication is derived from, for example, pBR322. The most useful yeast origin of replication is found in the extrachromosomal genetic element known as the 2 micron circle. The depiction of FIG. 5 shows that the novel vector contains the pBR322 origin of replication, a gene coding for ampicillin resistance in *E. coli*, a selectable yeast marker, trp 1 and the yeast 2μ origin of replication required for stable replication in yeast. The cDNA for coding of rotavirus surface antigen VP7, when inserted, is contained between the ADH promoter and terminator. The novel plasmid is capable of replication in either yeast or *E. coli*, and expression of surface antigen VP7 occurs when the plasmid is transfected into yeast.

Figure 6:
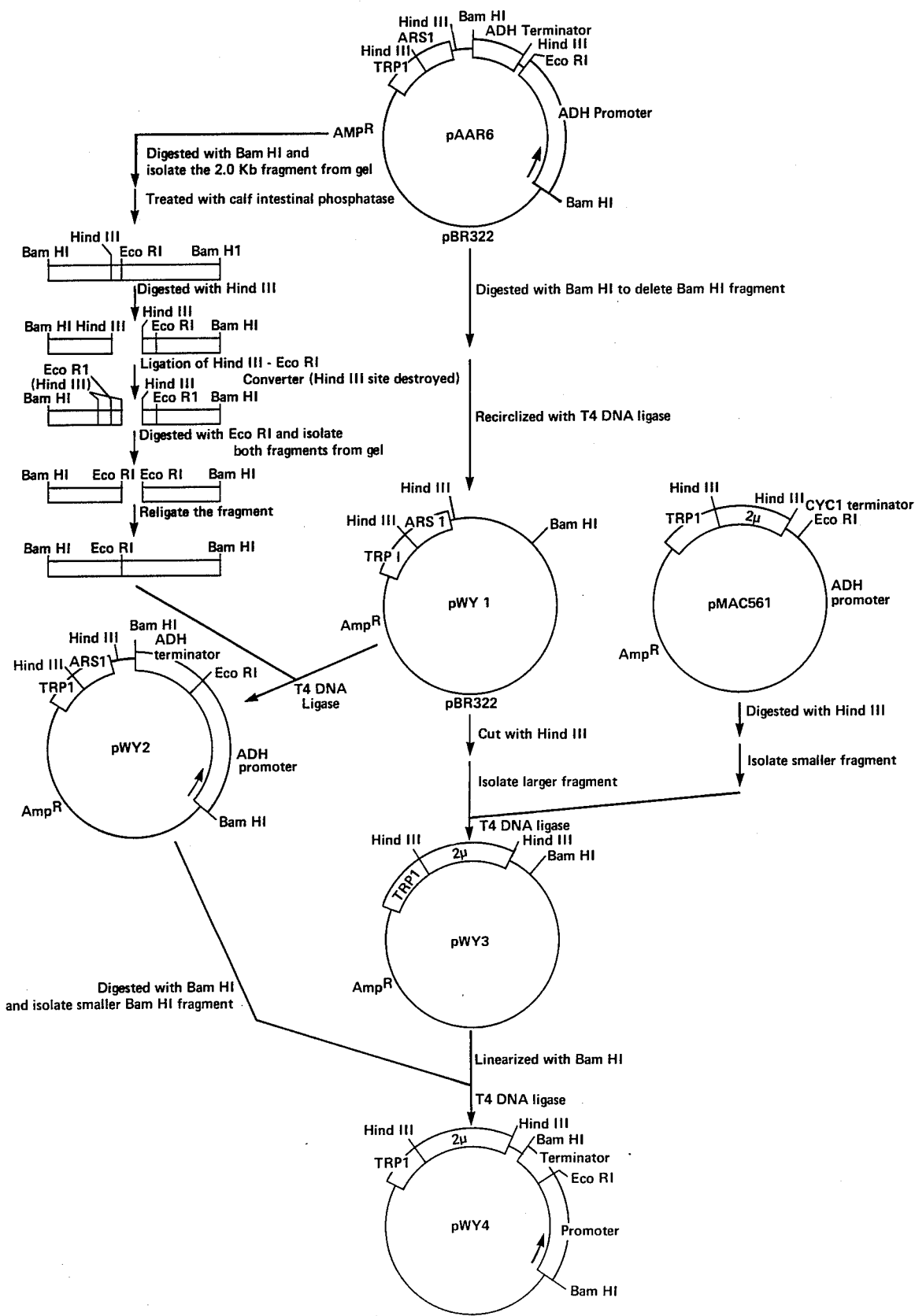
FIG. 6: depicts the construction of the yeast expression vector pWY4-3 of the invention.

The construction of the yeast expression plasmid of the invention is depicted in FIG. 6. The plasmid pAAR6, used in the construction of the novel plasmid of the invention, is obtained by the method disclosed by Ammerer, G., *Methods of Enzymology*, 101, 192–201 (1983). Plasmid pMAC561, also used in the construction of the novel plasmid of the invention, is disclosed in McKnight and McConaughy, *Proc. Natl. Acad. Sci. USA*, 80, 4412–16 (1983).

The polypeptidic surface antigen molecule elaborated by yeast transfected with the novel plasmid of the invention containing a cDNA sequence coding for human rotavirus WA strain surface antigen VP7 is useful in the production of pharmaceutical vaccine compositions active in imparting immunity in the host to infection by human rotavirus WA strain.

In the Examples that follow, the techinques, reactions and separation procedures are already well-known in the art. All enzymes, unless otherwise stated, are commercially available from one or more sources, such as Bethesda Research Laboratories (Gaithersburg, Md.) or New England Biolabs (Beverly, Mass.). Buffers and reaction conditions for restriction enzyme digestion were used according to recommendations supplied by the manufacturer for each enzyme, unless otherwise indicated. Standard methodology for other enzyme reactions, gel electrophoresis separations, and yeast and E. coli transformations may be found in Maniatis et al., *Molecular Cloning: Laboratory Manual*, Cold Spring Harbor Laboratory, Cold Spring Harbor, N.Y. (1982); Davis et al., *Advanced Bacterial Genetics*, Cold Spring Harbor Laboratory, Cold Spring Harbor, N.Y. (1980); and Sherman et al., *Methods in Yeast Genetics*, Cold Spring Harbor Laboratory, Cold Spring Harbor, N.Y. (1982).

The *E. coli* strain used for all plasmid manipulations is K12 strain 294 (ATCC No. 31446) (endo-A, thi−, hsi−, hsm+). The yeast strain is *Saccharomyces cerevisiae* 20B12 (α trp 1 pep 4-3) [Jones, T. *Genetics*, 85, 22–33 (1976)]. LB and M9a media for *E. coli* growth were prepared as described in Davis et al., *Advanced Bacterial Genetics*, supra. Yeast media YPD and SD were prepared according to Sherman et al., *Methods in Yeast Genetics*, supra.

EXAMPLE 1

Cloning of Gene 9 cDNA

A complementary DNA (cDNA) containing the rotavirus WA strain surface antigen VP7 coding sequences was prepared in the following manner:

Either total virion RNA (10 μg) or gene 9 RNA isolated by electroelution from a polyacrylamide gel was denatured for 2 minutes at room temperature in a reaction (30 μl) containing 10 mM tris-HCl (pH 7.9), 0.1 mM EDTA, and 10 mM methyl mercury hydroxide. After this the reaction volume was adjusted to 200 μl which contained 14 mM β-mercaptoethanol, 2μ/μl RNasin, 50 mM tris-HCl (pH 7.9), 10 mM $MgCl_2$, 200 mM NaCl, and 75 μm ATP. Then 20 units of poly A polymerase from *E. coli* (Sippel et al., *Eur. J. Biochem.,* 37, 31–40 (1973), was added for 2.5 minutes at 37° C. The polyadenylation reaction was stopped by extraction with phenol and RNA recovered from the aqueous phase by ethanol precipitation. An average of 30 adenylate residues per single-stranded RNA chain was added under these conditions.

The polyadenylated RNA was treated for 3 minutes at room temperature with 10 mM methyl mercury hydroxide. The reaction mixture was then diluted five-fold into a reaction volume of 200 μl that contained 50 mM tris-HCl (pH 8.3), 10 mM $MgCl_2$, 70 mM KCl, 10 mM dithiothretiol, 0.5 mM each of dATP, dCTP, dGTP and dTTP including 50° $C_i$ $^{32}$PdCTP (Amersham, 300 Ci/mmole), 100 μg/ml oligo $dT_{12-18}$, 0.5 U/ml RNAsin, and 1.05 U/ml AMV reverse transcriptase. After 1 hour at 42° C. the reaction mixture was extracted with phenol and chloroform, the aqueous phase adjusted to 0.3N NaOH, and incubated 16 hours at 37° C. After neutralization, DNA was recovered and annealed 1 hour at 68° C. in 20 mM tris-HCl (7.5), 1 mM EDTA, 0.2 M NaCl followed by slow cooling to room temperature. DNA was then repaired using either AMV reverse transcriptase as above or th Klenow fragment of DNA polymerase 1 (Davis et al., Gene, 10, 205–218 (1980). This DNA was then fractionated on a 2.4% alkaline agarose gel (McDonnell et al., 1977) and the DNA of approximately 1000 bp was eluted, tailed with dC residues by terminal transferase (Davis et al., Gene, 10, 205–18 (1980)) and cloned in pBR322 that had been cut with PstI and tailed with dG residues.

The Rotavirus gene 9 cDNA was cloned in two separate clones. Clone R*1-6* contained the 5′-end half of the genome, while clone R2–34 contained the 3′-end half of the genome. There are about 150 bp overlapping sequences in the middle of the gene. The complete NA sequence was determined by Maxam and Gilbert technique (FIG. 1).

EXAMPLE 2

Reconstruction of Rotavirus Gene 9

Prior to ligating the two halves of the genome together, the 5′- and 3′-ends are edited to remove extraneous sequences, in particular the poly A and poly C tails which were attached to each end of the molecule during cloning of the cDNA.

(a) Editing of the 5′-end of rotavirus gene 9

The R1-6 plasmid containing 5′-end half of rotavirus gene 9 DNA was digested with restriction endonuclease DraI and the DraI fragment purified from low melting agarose. Bam HI linker (CGGATCCG) was blunt-end ligated onto the DraI fragment. After digestion with Bam HI, it was cloned into plasmid pBR322 at the Bam HI site. This Bam HI fragment was subsequently purified and Bam HI EcoRI converter (GTACCGAATTCG) attached to the end by $T_4$DNA ligase. It was then cloned into the EcoRI site of plasmid pBR325. This recombinant plasmid was then digested with SacI and ClaI and the SacI-ClaI fragment from pR1–6 was inserted into this vector. This manipulation reconstitutes the 5′-end half of the rotavirus gene 9. The first 6 nucleotides of rotavirus gene was removed in this construction. The EcoRI-ClaI fragment containing the rotavirus gene 9 DNA was used for the reconstruction of a complete gene (FIG. 2).

(b) Editing of the 3′-end of rotavirus gene 9

Plasmid pR2-34 containing the 3′-end half of rotavirus gene 9 was digested with restriction endonuclease PvuI. The linearized DNA was treated with Bal31 at 30° C. for approximately 20 seconds and the reaction was stopped by the addition of EDTA to a final concentration of 40 mM, followed by phenol/chloroform extraction and ethanol precipitation of the Ba131-treated DNA. This DNA was then treated with DNA polymerase I (Klenow fragment) in 50 mM Tris-HCl (pH 7.2), 10 mM $MgSO_4$, 0.1 mM dithiothreitol and 100 μM each of deoxynucleotide. Following the addition of EcoRI linker (GGAATTCC) to both ends. The DNA was digested with EcoRI and then re-circlized with T4 DNA ligase. This re-circlized DNA was used to transform *E. coli* 294 and the transformants screened for plasmid having the shortest 3′-end untranslated DNA. Clone no. A24-3 contains rotavirus DNA up to three basepairs beyond termination codon TAG. This clone was used for the reconstruction of rotavirus gene 9 (FIG. 3).

c. Reconstruction of rotavirus gene 9

The EcoRI-ClaI 0.6 Kb fragment of the 5′-end of gene 9 was ligated to the ClaI-EcoRI 0.4 Kb fragment of the 3′-end of gene 9 with T4 DNA ligase in vitro. The 1 Kb fragment was isolated and the complete gene 9 sequence was inserted into yeast expression vector pWY4-3. The vector was used to transform *E. coli* and the transformants were screened for those yielding recombinant plasmids having the gene 9 inserted in both orientations.

EXAMPLE 3

Construction of Yeast Vectors Active in the Expression of Human Rotavirus Strain WA Surface Antigen VP7

A plasmid vector (pWY4-3) for the expression of human WA rotavirus surface antigen VP7 in yeast was constructed as depicted in FIG. 6.

The yeast expression vector, pWY4-3, is essentially derived from pAAR6. This yeast vector carries Trpl gene as a selectable yeast marker and yeast 2μ origin for stable replication in yeast. It also carries ampicillin resistance gene and origin of replication from pBR322 for amplication in *E. coli*. The yeast plasmid pAAR6 contains the desired promoter and terminator from a yeast gene coding for alcohol dehydrogenase. However, its origin of replication (arsl) was isolated from yeast chromosome, and plasmids carrying the arsl chromosomal origin are not stable in yeast. Thus, the first modification of pAAR6 involved the replacement of the chromosomal origin of replication by the yeast 2μ origin from plasmid pMAC561. The latter is digested with Hind III and the smaller fragment so obtained is isolated. The plasmid pWY1 (derivative of pAAR6) is likewise digested with Hind III and the larger fragment obtained thereby is isolated. The two isolated fragments are mixed and ligated wtih T4 DNA ligase and *E. coli* 294 is transformed with the plasmid, pWY3, so obtained.

The second modification of pAAR6 involved the replacement of the 100 basepair EcoRI-Hind III fragment derived from 2μ DNA connecting the ADHI promoter and terminator with a Hind III-EcoRI converter (AGCTCGAATTCCG) with concomitant elimination of the Hind III site. Thus, pAAR6 is digested with BamHI and a 2.0 Kb fragment is isolated from gel. The fragment is treated with calf intestine phosphatase and then digested with Hind III. The smaller of the two resulting subfragments so obtained is ligated with Hind III→EcoRI converter. Both subfragments are then digested with EcoRI and isolated from gel. The subfragments are re-ligated. Plasmid pWY3 is then digested with BamHI and re-ligated with the modified ADHI promoter and terminator sequence obtained, supra. The resulting plasmid, pWY4-3, replicates stably in yeast and expression of foreign genes therein is driven by the promoter sequence from yeast ADHI gene.

In the final construct, the modified and reconstructed gene 9 is inserted into yeast expression vector pWY4-3 to obtain plasmid pS20-2-3, which is depicted in FIG. 4.

EXAMPLE 4

Synthesis of Rotavirus Gene 9 Product in Yeast

Figure 7:
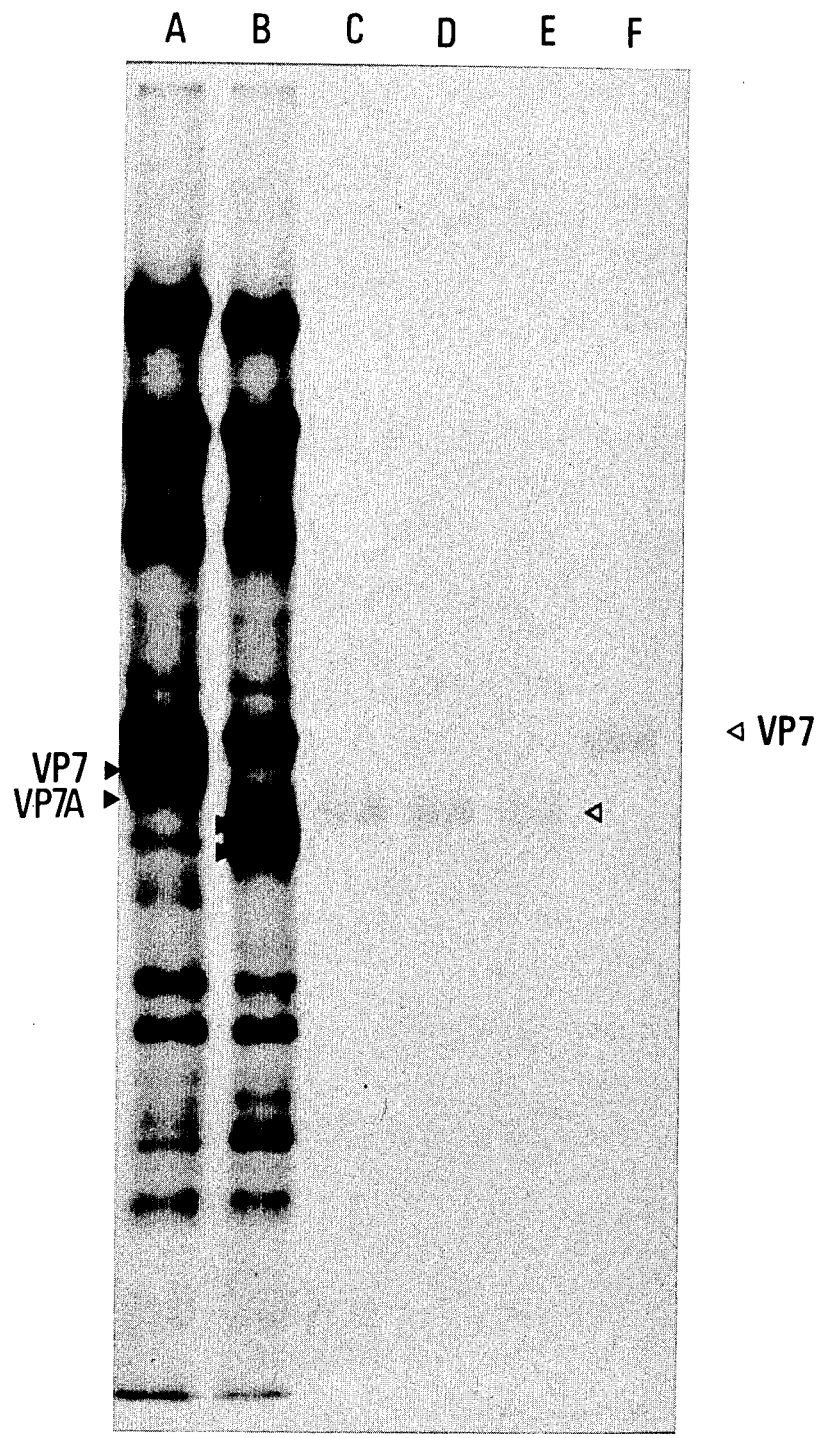
FIG. 7: depicts the production of glycosylated human WA rotavirus gene 9 polypeptide in yeast.

Transformation of yeast strain 20B12 was carried out as described by Hsiao and Carbon, *Proc. Natl. Acad. Sci. USA*, 76, 3829–33 (1979). *Saccharomyces cerevisiae* strain 20B12 containing expression vector pS20-2-3 has been deposited with the American Type Culture Collection under accession number 20910. Trp+ transformants were selected on yeast minimal medium plate. Yeast transformants for protein labeling were prepared as follows: yeast cells were grown to $2 \times 10^7$ cells per ml in SD medium supplemented with 1% casamino acids. After a single wash with SD medium, samples were resuspended in one tenth of the original volume of SD containing all amino acid mix except methionine. $^{35}$S-methionine was added to 250 μCi/ml and the culture was incubated at 30° C. for 60 minutes. The labeled cells were pelleted and washed with phosphate-buffered saline (PBS). Then the labeled samples were broken up in 0.5 ml of PBS with 1.5 gm of sterile glass beads. The lysed cultures were then treated with RIPA buffer for immunoprecipitation by guinea pig antirotavirus WA strain antisera [Mason et al., *J. Virology*, 33, 1111–21 (1980)] and analyzed by acrylamide gel electrophoresis [Lammeli, *Nature*, 227, 680–85 (1979)]. FIG. 7 shows that the transformed yeast cells produce human rotavirus strain WA surface antigen VP7. The yeast-produced VP7 is glycosylated. Both glycosylated (lane F) and de-glycosylated (treated with endoglycosidase H, lane CDE) VP7 are comparable in size to that of purified rotavirus (lane A) and de-glycosylated rotavirus (lane B).

What is claimed is:

1. The *Saccharomyces cerevisiae* expression vector pWY4-3 which comprises a DNA sequence coding for the human WA rotavirus surface antigen VP7 and which vector when transformed into a suitable *Saccharomyces cerevisiae* strain confers upon said strain the ability to produce glycosylated human WA rotavirus surface antigen VP7.

2. A biologically pure culture of the yeast *Saccharomyces cervisiae* 20B12, which carries the expression vector of claim 1.

* * * * *